United States Patent
Lu

(10) Patent No.: US 11,795,206 B2
(45) Date of Patent: Oct. 24, 2023

(54) SPECIFIC BIFUNCTIONAL BY-001 (ACTIVE COMPOSITION OF HOMOMULTIMER OF CHIMERIC PROTEIN PD-L1 / FC-GAMMA1) DOWN REGULATES THE ACTIVATION OF HUMAN IMMUNE CELLS AND THE USE THEREOF

(71) Applicant: Yunbiao Lu, North Potomac, MD (US)

(72) Inventor: Yunbiao Lu, North Potomac, MD (US)

( * ) Notice: Subject to any disclaimer, the term of this patent is extended or adjusted under 35 U.S.C. 154(b) by 60 days.

(21) Appl. No.: 16/190,641

(22) Filed: Nov. 14, 2018

(65) Prior Publication Data
US 2019/0241643 A1 Aug. 8, 2019

Related U.S. Application Data

(60) Provisional application No. 62/689,214, filed on Jun. 24, 2018.

(51) Int. Cl.
| | | |
|---|---|---|
| C07K 14/705 | (2006.01) | |
| A61K 35/17 | (2015.01) | |
| A61P 37/06 | (2006.01) | |
| C07K 14/735 | (2006.01) | |
| A61K 47/68 | (2017.01) | |
| A61K 38/00 | (2006.01) | |

(52) U.S. Cl.
CPC ........ *C07K 14/70596* (2013.01); *A61K 35/17* (2013.01); *A61K 47/6811* (2017.08); *A61P 37/06* (2018.01); *C07K 14/70532* (2013.01); *C07K 14/70535* (2013.01); *A61K 38/00* (2013.01); *C07K 2319/30* (2013.01)

(58) Field of Classification Search
None
See application file for complete search history.

(56) References Cited

U.S. PATENT DOCUMENTS

| | | |
|---|---|---|
| 2015/0203579 A1 | 7/2015 | Papadopoulos et al. |
| 2015/0361155 A1 | 12/2015 | Tykocinski |
| 2017/0189476 A1 | 7/2017 | Sung et al. |
| 2018/0334504 A1* | 11/2018 | Qu ........................ A61P 35/00 |

FOREIGN PATENT DOCUMENTS

WO 2017201131 A1 11/2017

OTHER PUBLICATIONS

Definition of the word "treat"—The Britannica Dictionary online (2023), 2 pages.*
Rosales C (2017) Fcγ Receptor Heterogeneity in Leukocyte Functional Responses. Front. Immunol. 8: 280; 1-13.*
NCBI Accession Q9NZQ7 (2022), 9 pages.*
NCBI Accession AAG00909 (2016), 3 pages.*
Liu et al. (2015) Soluble PD-1 aggravates progression of collagen-induced arthritis through Th1 and Th17 pathways. Arthritis Research & Therapy 17: 340; 1-13.*
Song et al. (2015) Protective effects of Fc-fused PD-L1 on two different animal models of colitis. Gut 64: 260-271.*
Kim et al. (2016) Programmed cell death ligand 1 alleviates psoriatic inflammation by suppressing IL-17A production from programmed cell death 1-high T cells. J Allergy Clin Immunol 137: 1466-1476.*
Tian et al. (2016) The PD-1/PD-L1 inhibitory pathway is altered in pre-eclampsia and regulates T cell responses in pre-eclamptic rats. Scientific Reports 6: 27683; 1-14.*
Wan et al. (2018) A Tolerogenic Artificial APC Durably Ameliorates Experimental Autoimmune Encephalomyelitis by Directly and Selectively Modulating Myelin Peptide-Autoreactive CD4+ and CD8+ T Cells. J Immunol 201: 1194-1210.*
Beswick et al. (2018) Expression of Programmed Death-Ligand 1 by Human Colonic CD90+ Stromal Cells Differs Between Ulcerative Colitis and Crohn's Disease and Determines Their Capacity to Suppress Th1 Cells. Front. Immunol. 9: 1125; 1-15.*
Miao et al. (2018) PD-L1 reverses depigmentation in Pmel-1 vitiligo mice by increasing the abundance of Tregs in the skin. Scientific Reports 8: 1605; 1-6.*
Jiang et al. (2018) PD-1/PD-L1 regulates Treg differentiation in pregnancy-induced hypertension. Brazilian Journal of Medical and Biological Research 51(8): e7334; 1-8.*
Singh et al. (2011) Role of PD-L1 and PD-L2 in allergic diseases and asthma. Allergy 66: 155-162.*
Zhou et al. (2016) Treatment of murine lupus with PD-L1g. Clinical Immunology 162: 1-8.*
Dong et al. (1999) B7-H1, a third member of the B7 family, co-stimulates T-cell proliferation and interleukin-10 secretion. Nature Medicine 5: 1365-1369.*
Bournazos et al. (2017) The role and function of Fcγ receptors on myeloid cells. Microbiol Spectrum 4(6): MCHD-0045-2016; 1-19.*
Levin et al. (2015) Fc fusion as a platform technology: potential for modulating immunogenicity. Trends in Biotechnology 33(1): 27-34.*
Yu et al. (2016) Targeting FcγRs to treat antibody-dependent autoimmunity. Autoimmunity Reviews 15: 510-512.*

(Continued)

*Primary Examiner* — Ilia I Ouspenski
(74) *Attorney, Agent, or Firm* — NKL Law; Allen Xue

(57) ABSTRACT

An active form (BY-001) of a homomultimeric chimeric protein PD-L1/Fc-gammal may have a composition of 25% dimer, 30% tetramer and 45% hexamer. BY-001 consists of two distinct functional domains at the aggregated state, one is the extracellular domain of PD-L1 and another one is the IgG1 Fc region. Accordingly, the first functional domain of PD-L1 at its aggregated state is more effective in suppressing the activity of CD3+ and CD28+ T cells; while, on the other hand, the second functional domain of FC-gammal at its aggregated state exerts only the suppressive effects on the immune cell bearing the Fc-gamma receptors. Thus, the features provided in present invention indicate that BY-001 regulates the functions of immune cells subsets that are responsible for the peripheral immune tolerance, which makes BY-001 potential to help restore or maintain the peripheral immune tolerance in patients with autoimmune diseases or in recipients of allografts.

6 Claims, 11 Drawing Sheets
Specification includes a Sequence Listing.

(56) References Cited

OTHER PUBLICATIONS

Zuercher et al. (2016) IVIG in autoimmune disease—Potential next generation biologics. Autoimmunity Reviews 15: 781-785.*

Song, Mi-Young et al.; Protective effects of Fc-fused PD-L1 on two different animal models of colitis, Gut, vol. 64, 2014-06-05, pp. 260-271.

Iao, Wenjun et al.; The Systemic Activation of Programmed Death 1-PD-L1 Axis Protects Systemic Lupus Erythematosus Model from Nephritis, American Journal of Nephrology, 2017;46:371-379.

Wang, Chia-Jen et al.; Protective Role of Programmed Death 1 Ligand 1 (PD-L1) in Nonobese Diabetic Mice -- The Paradox in Transgenic Models, DIABETES, vol. 57, pp. 1861-1869, Jul. 2008.

Nakamura, Akira et al.; A role of FcγRIIB in the development of collagen-induced arthritis, Biomedicine & Pharmacotherapy 58 (2004) 292-298, 2004-04-23.

Callaghan, Chris J et al.; Regulation of Allograft Survival by Inhibitory FcγRIIb Signaling, The Journal of Immunology, 2012; 189:5694-5702, 2012-11-12.

Roghanian, Ali et al.; New revelations from an old receptor: Immunoregulatory functions of the inhibitory Fc gamma receptor, FcγRIIB (CD32B), Journal of Leukocyte Biology, 2018;103:1077-1088.

* cited by examiner

Fig. 1. Design for Chimeric Peptide of PD-1L/Fc-gamma1 (BY-001) and It's Amino Acid Sequence

A.

Human PD-L1 domain    Human IgG1Fc

| sig | V-set | C-set | IgG1Fc |

B. SEQ ID NO:2

```
1    MRIFAVFIFMTYWHLLNAFTVTVPKDLYVVEYGSNMTIECKFPVEKQLDLAALIVYWEMED
62   KNIIQFVHGEEDLKVQHSSYRQRARLLKDQLSLGNAALQITDVKLQDAGVYRCMISYGGAD
123  YKRITVKVNAPYNKINQRILVVDPVTSEHELTCQAEGYPKAEVIWTSSDHQVLSGKTTTNS
185  KREEKLFNVTSTLRINTTTNEIFYCTFRRLDPEENHRSDKTHTCPPCPAPELLGGPSVFLFPP
248  KPKDTLMISRTPEVTCVVVDVSHEDPEVKFNWYVDGVEVHNAKTKPREEQYNSTYRVVSV
308  LTVLHQDWLNGKEYKCKVSNKALPAPIEKTISKAKGQPREPQVYTLPPSREEMTKNQVSLTC
370  LVKGFYPSDIAVEWESNGQPENNYKTTPPVLDSDGSFFLYSKLTVDKSRWQQGNVFSCSV
430  MHEALHNHYTQKSLSLSPGK 449
```

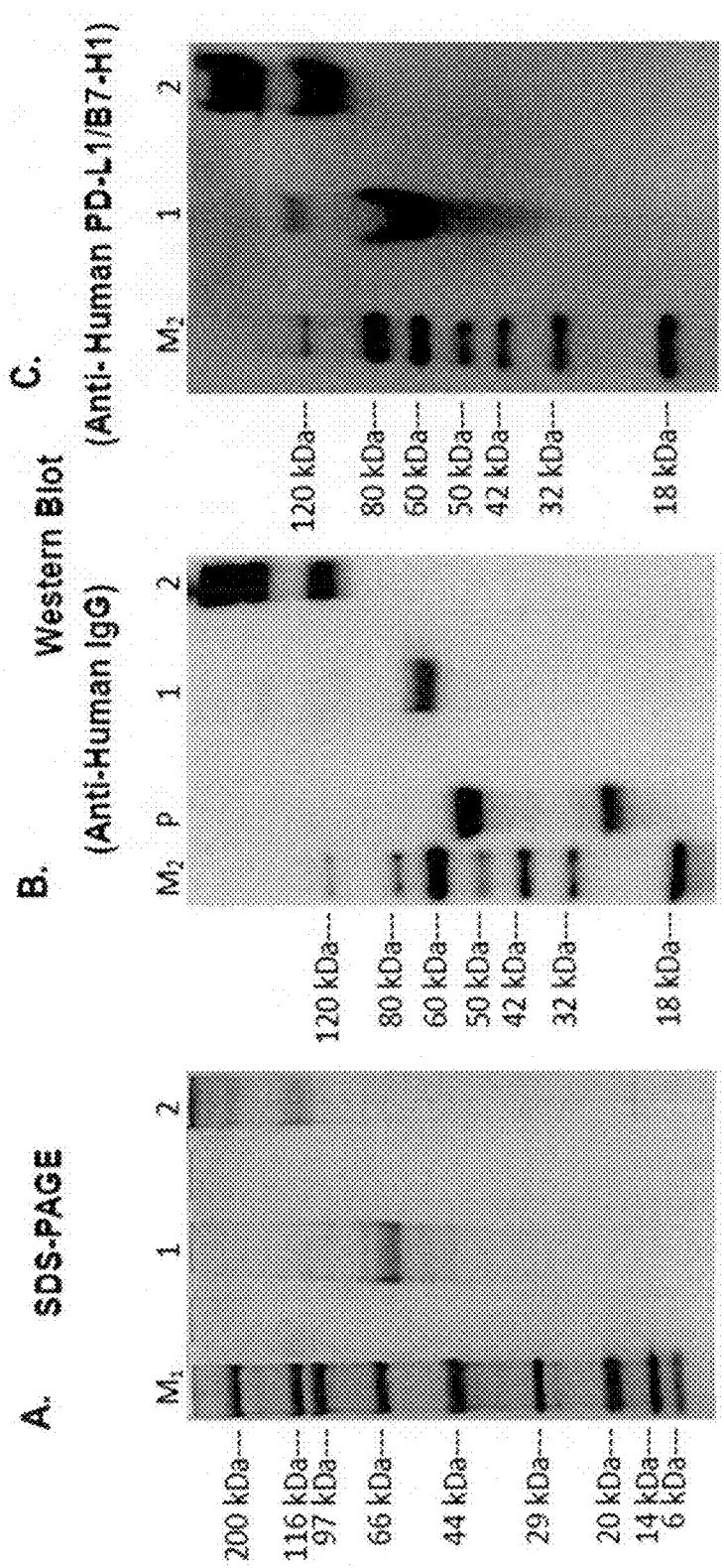
Fig. 2. Visualized Protein of BY-001 on SDS-Page Gel and Western-Blot

Fig. 2. Visualized Protein of BY-001 on SDS-Page Gel and Western-Blot

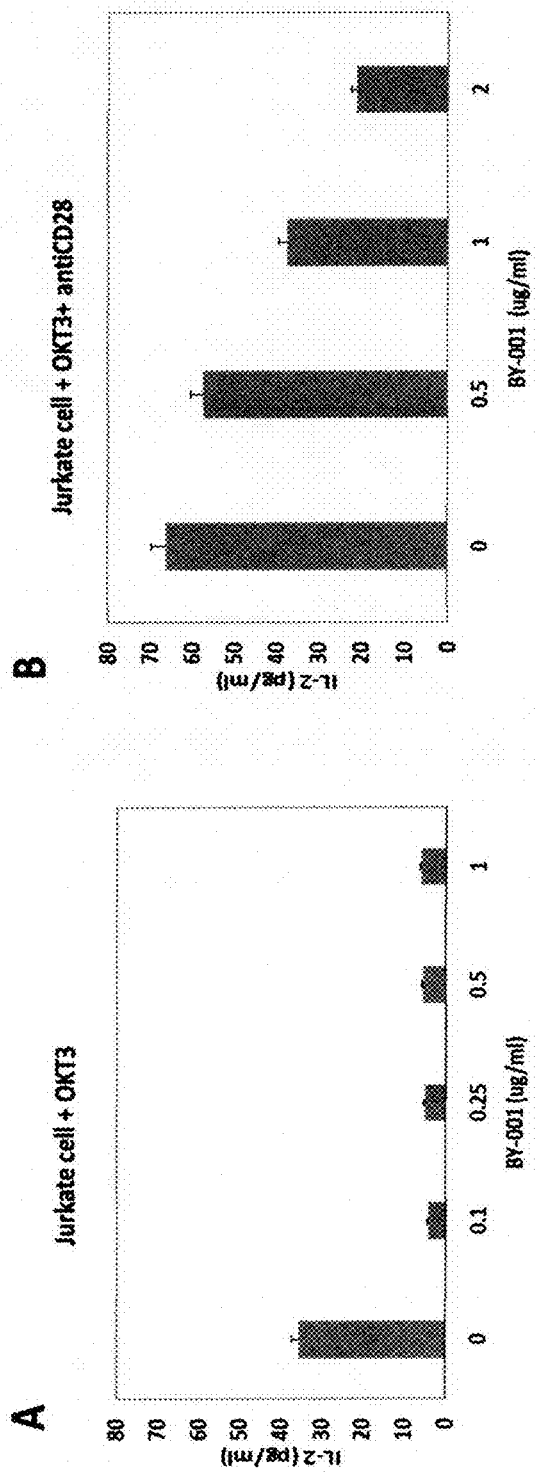
Fig. 3 BY-001 suppresses IL-2 production from Jurkate cell line

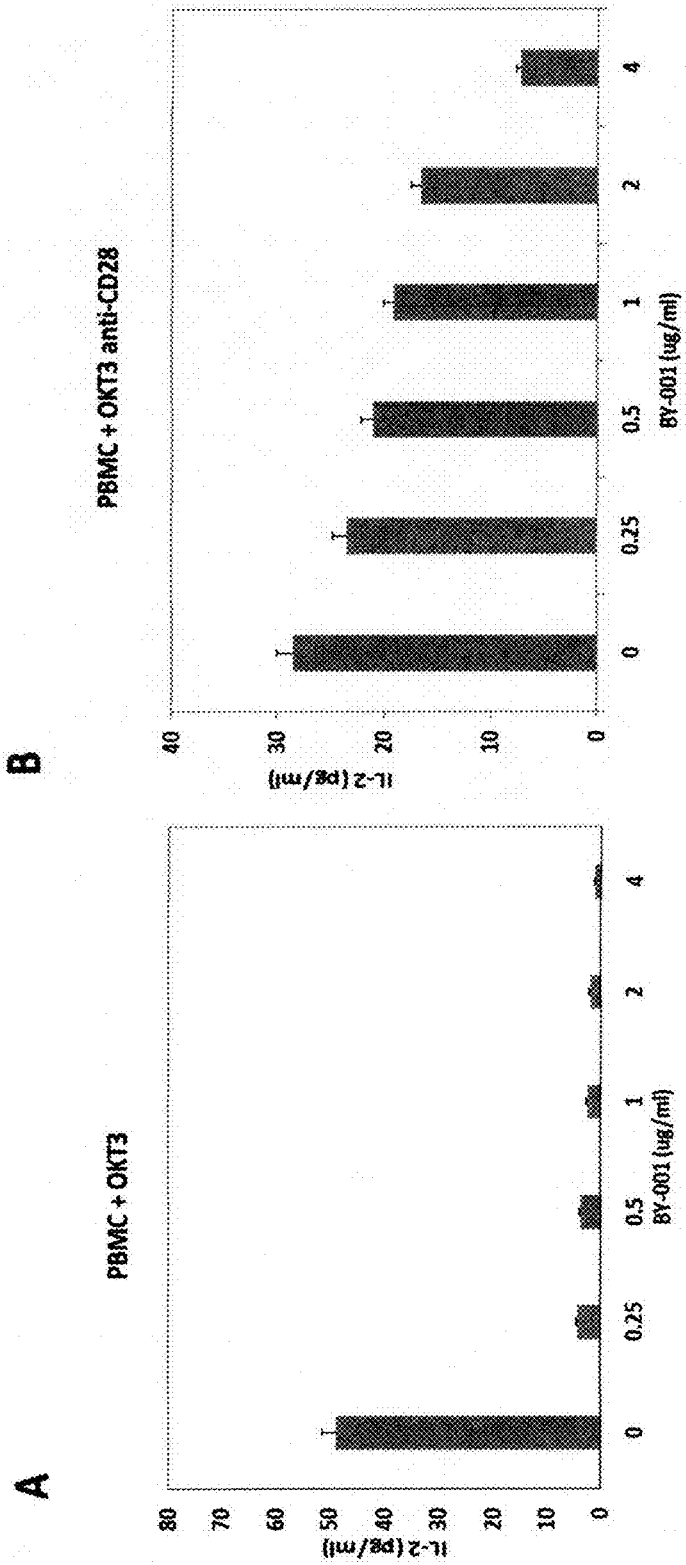
Fig. 4 BY-001 suppresses IL-2 production from PBMC human primary cells

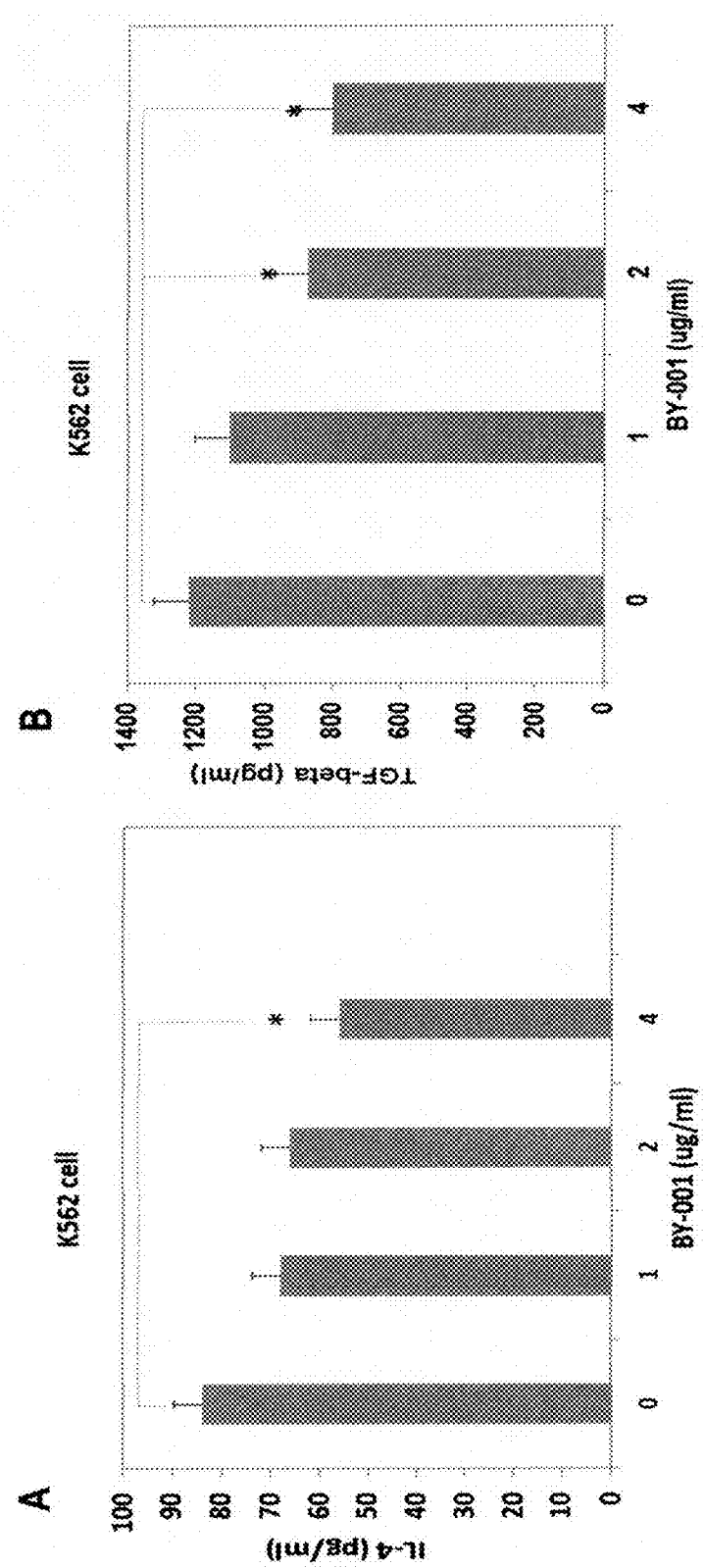

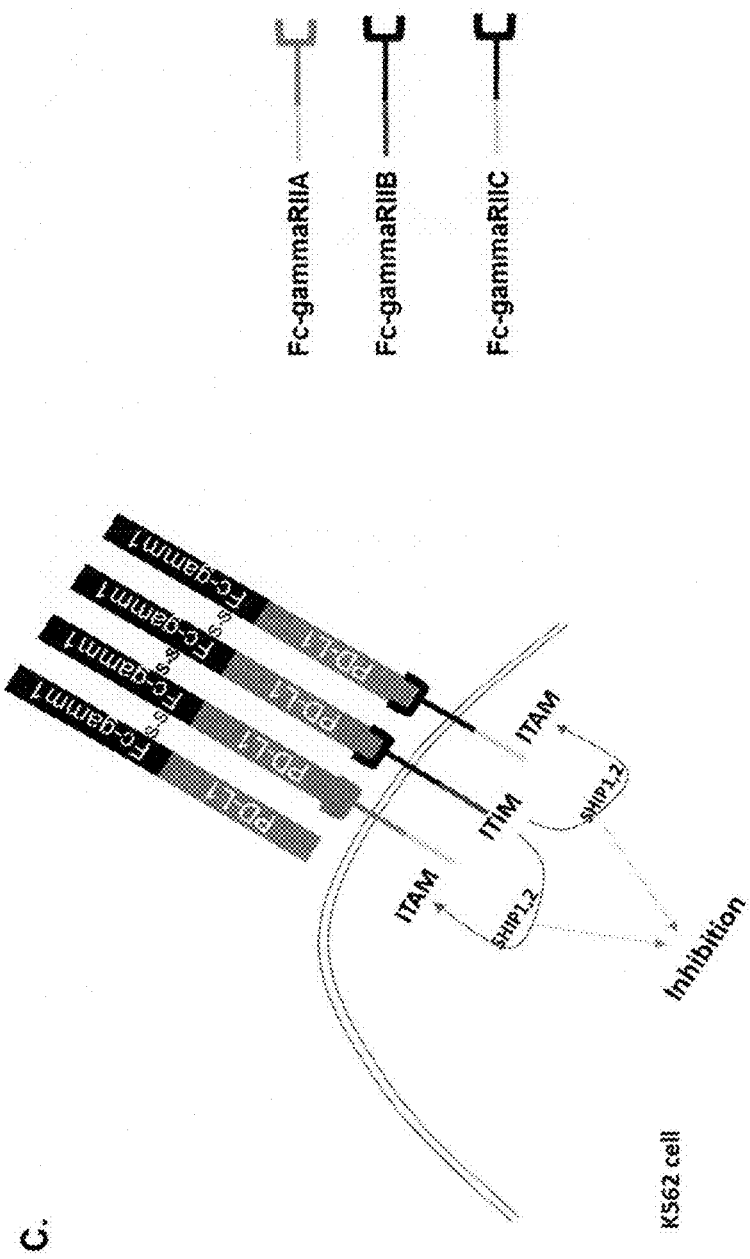
Fig. 5 BY-001 regulates IL-4 and TGF-beta production from K562 cell

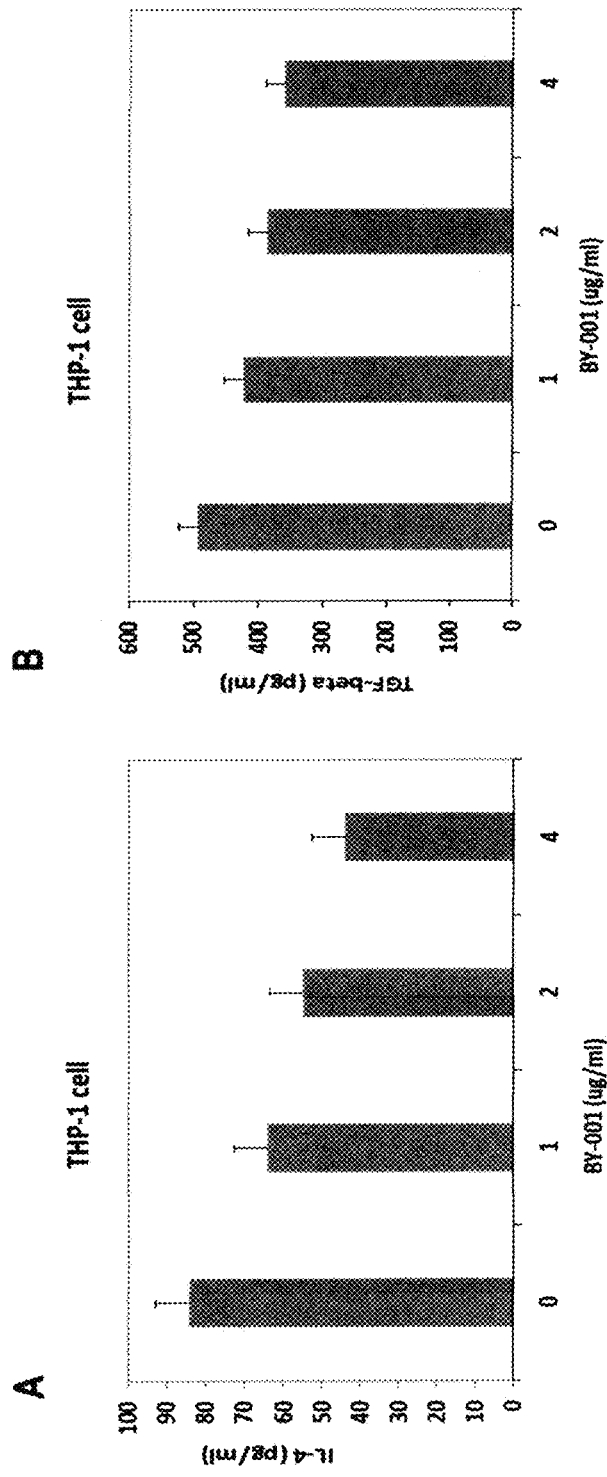
Fig. 6 BY-001 regulates IL-4 and TGF-beta production from THP-1 cell

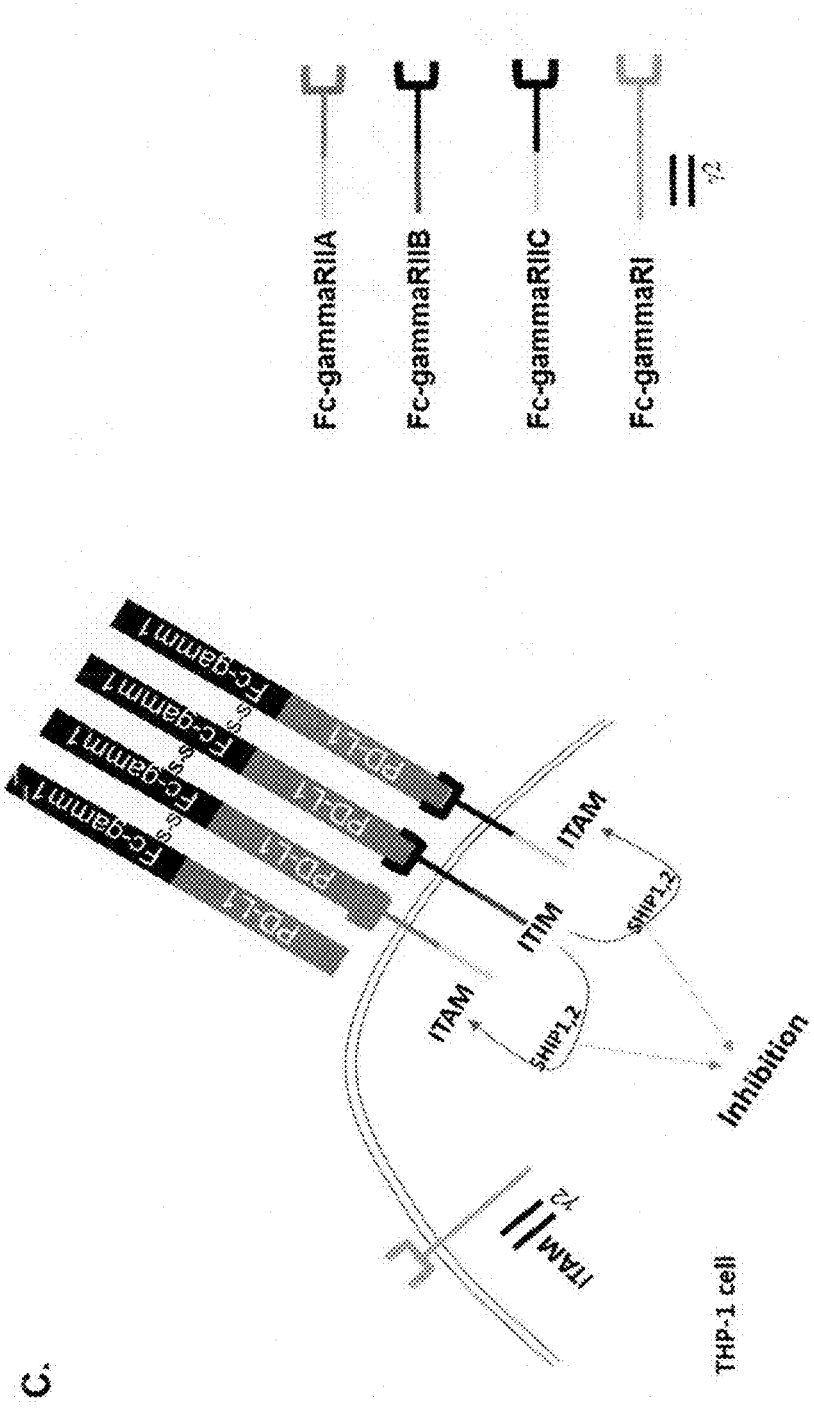
Fig. 6 BY-001 regulates IL-4 and TGF-beta production from THP-1 cell

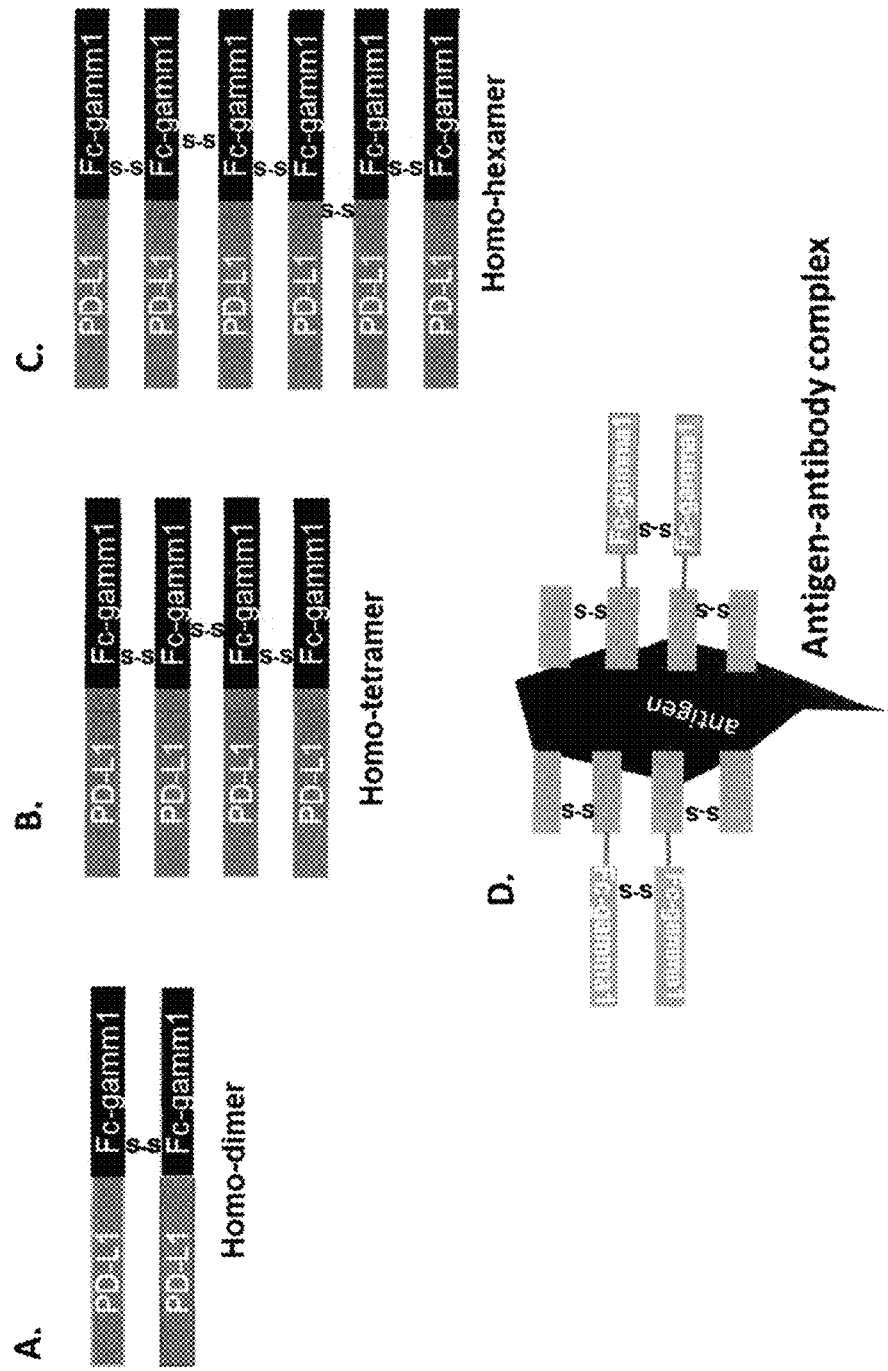
Fig. 7 Advanced structural difference between BY-001 and antigen-antibody complex

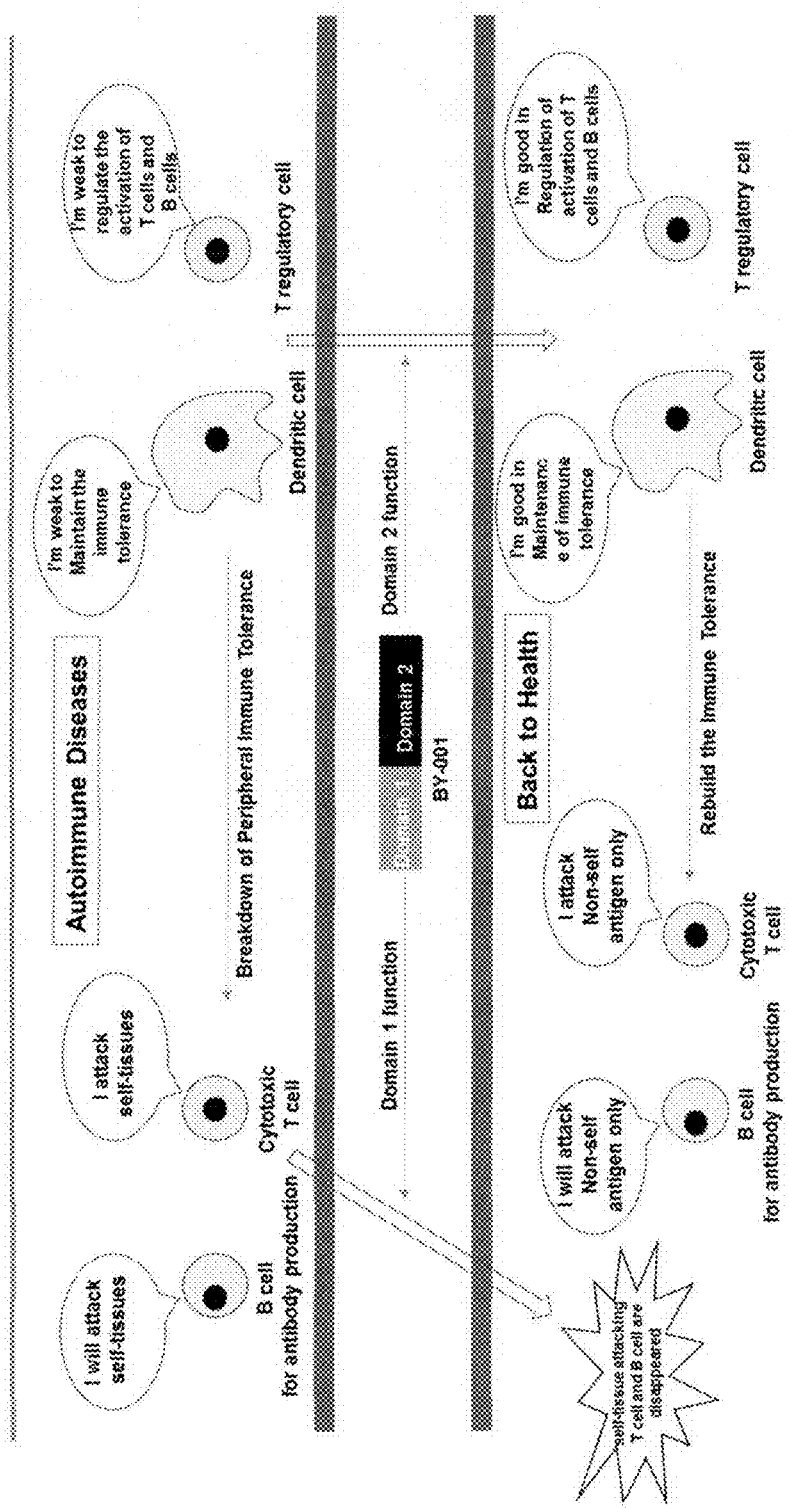

SPECIFIC BIFUNCTIONAL BY-001 (ACTIVE COMPOSITION OF HOMOMULTIMER OF CHIMERIC PROTEIN PD-L1 / FC-GAMMA1) DOWN REGULATES THE ACTIVATION OF HUMAN IMMUNE CELLS AND THE USE THEREOF

INCORPORATION OF SEQUENCE LISTING

This application contains a sequence listing submitted in Computer Readable Form (CRF). The CFR file containing the sequence listing entitled "BY-001sequence_ST25.txt", which was created on Oct. 21, 2022, and is 6,230 bytes in size. The information in the sequence listing is incorporated herein by reference in its entirety.

1. BACKGROUND OF THE INVENTION

The immune system normally recognizes and defends against foreign pathogens but does not respond to self-components of tissues, such intrinsic state is established and maintained precisely by the process of immune tolerance. The inflammatory damage of one or more organ systems caused by inappropriate activation of self-reactive both or either T cells and B cells is due to the loss of balance between effectors (B cells and T cells) [1, 2] and regulatory components (Treg cells and dendritic cells) of the immune system [3]. Therefore, restoration of immune tolerant state is the ultimate goal in the treatment of autoimmune diseases [4, 5].

Cell surface molecules such as CTLA-4 (cytotoxic T-lymphocyte-associated protein 4, or CD152) and PD-1 (Programmed Death-1, also known as CD279) deliver inhibitory immunoregulatory signals that are thought to be crucial to the maintenance of normal immune tolerance [6, 7] through its recognizing and binding to CD80 (B-7.1) or CD86 (B-7.2). Based on the discoveries, Bristol-Myers Squibb, a pharmaceutical company, developed a chimeric protein composed of the Fc region of the immunoglobulin IgG1 and the extracellular domain of CTLA-4 named as Abatacept (CTLA-4/Fc), thereafter, it was approved for clinic application by FDA in 2011. However, the pharmacological mechanism of Abatacept is to serve as antagonist of CD28 to interrupt the second signal, CD28 binding to B-7 for TCR activation, instead of the delivery of checkpoint signal through CTLA-4. Therefore, Abatacept interrupts the systemic cellular immune response, which, as a side effect, may cause serious infectious diseases, even cancer.

Second cell surface molecule responsible for immune checkpoint is PD-1 (Programmed cell death protein 1, also known as CD279), which is strictly expressed on thymocytes, activated T cells and pro-B cells. It has been believed that PD-1 is related biasedly to the maintenance of peripheral immune tolerance when it is associated with either of its two identified ligands: 1), Programmed Death-1 ligand 1 (PD-L1), also known as CD274 or B7-H1, broadly expressed on the hematopoietic and nonhematopoietic cells including tumor cells; 2), Programmed Death-1 ligand 2 (PD-L2), also known as CD273, or B7-DC strictly expressed on the dendric cells and macrophages. The PD-1 engagement with PD-Ls results in suppressing the activation of T cell or differentiation of mature B cell. Thus far three mechanisms have been elaborated for the pivotal role of PD-1/PD-L1 pathway in immune tolerance: (1) Induction of T cell anergy [8] through PD-L1 binding to PD-1 then activating the SHP2 to suppress the TCR/CD28 signaling; (2) suppression of B cell maturation through PD-L1 binding to PD-1 expressed on pre-B cells then activating the SHP2 to suppress the BCR signaling; [9]; (3) generation of regulatory T cells (especially type 1 (Tr1)) [10] and conversion of human TH1 into Treg cell (iTreg cell) [11]. In addition, soluble forms of PD-1 (sPD-1) and PD-L1 (sPD-L1) in peripheral blood may also be a source for the regulatiOn of PD-1/PD-L1 pathway in immunity [12, 13]. A perfect manifestation of such mechanisms is that certain tumor cells use PD-L1 overexpression on their cell membranes and simultaneously shed into the circulation to successfully escape immune attacks [14].

In contrary with in tumor, according to the latest findings in autoimmune diseases, the weakening or deletion of the PD-1/PD-L1 pathway in immune cells is directly related to the instability or destruction of peripheral immune tolerance [10]. Mounting evidence demonstrate that impaired PD-1/PD-L1 function plays an important role in a variety of autoimmune diseases, such as SLE (systemic lupus erythematosus) and RA (Rheumatoid Arthritis), etc. [15]. The animal model demonstrates that loss of signaling of PD-1/PD-L1 (PD-1 knockout mice) develops lupus-like autoimmune disease [16], or autoimmune dilated cardiomyopathy depending upon the genetic background [17]. PD-L1 deficiency enhances disease progression in the experimental autoimmune encephalomyelitis [18], nonobese diabetic (NOD) model of autoimmune diabetes [19, 20] and the murine model of multiple sclerosis (MS)[21]. Tissue expression of PD-L1 mediates peripheral T cell tolerance [22].

The third cell surface molecule responsible for immune tolerance is Fc-gamma receptor type IIB (one of Fc-gammaRIIA/B, collectively known as CD32). Human Fc-gamma receptors have been identified so far are hFc-gammaRI (CD64), hFc-gammaRll (types A and B, collectively known as CD32) and hFc-gammaRIII (types A and B, collectively known as CD16). Each type of receptor exhibits distinctive tissue distribution, structure and binding specificity towards various IgG subclasses (7,8). Fc-gammaRIIB is restrict expressed on B cell, monocyte/macrophage and dendritic cell in human, while basophil, eosinophil and mast cell as well in mice. Fc-gammaRII displays low affinity for monomeric IgG but high-avidity for aggregated multimeric IgG, which are particularly important in the recognition and binding of antibody—antigen complexes during an immune response [23]. The B cell stage(s) at which Fc-gammaRllB exerts its function as a gatekeeper of self-tolerance has recently been defined [24, 25]. The main function of Fc-gammaRIIB is to inhibit activating signals, which is achieved through co-ligation of Fc-gammaRIIB with either activating Fc-gammaRs or with the BCR by immune complexes ([26]). This leads to phosphorylation of the cytoplasmic domain ITIM of Fc-gammaRllB by the Src-family kinase IYN. This phosphorylation event is thought to require access of Fc-gammaRIIB to sphingolipid rafts in which activating Fc-gammaRs and the BCR reside following cross-linking. Subsequent binding of SH2-domain-containing inositol phosphatases (SHIPs), in particular SHIP 1, result in the dephosphorization of downstream targets and inhibition of the activating signaling cascade. There is accumulating evidence that Fc-gammaRllB mediates its function during late stages of B cell maturation, thus representing a distal checkpoint [25]. Through the analysis of an anti-DNA knock-in model, it was established that the absence of Fc-gammaRIIB resulted in the expansion of IgG-positive plasma cells secreting autoreactive antibodies (Fukuyama et al., 2005). Here, Fc-gammaRIIB might serve as the final barrier to prevent these B cells with potentially harmful BCR specificities from maturing into plasma cells that would otherwise induce tissue pathology by secretion of large amounts of self-reactive antibodies. Another cell type where Fc-gamagRIIB may play an important role in regulating immunity and tolerance are the dendritic cells [27-29]. A number of chronic inflammatory diseases have been shown to be associated with Fc-gamma receptor genetic variants and include (but are not limited to) autoimmune pathologies, such as systemic lupus erythematosus (SLE) [30], rheumatoid arthritis[31], acute allograft rejection [32] and vascular inflammatory and thrombotic disorders, such as coronary artery stenosis, peripheral atherosclerosis and vasculitis [33, 34].

Since PD-1 is expressed in activated T cells and B cells, it is expected that the PD-L1 protein can be effectively used as a therapeutic agent that specifically targets activated immune cells to suppress the inflammatory reaction not only in an autoimmune disease but also in organ transplantation. However, Fc-gammaRIIB is expressed in dendritic cells and monocytes/macrophages, it is expected also that aggregated form of Fc-gammal can be used as a therapeutic agent that specifically targets these immune cells to suppress the inflammatory reaction during the autoimmunity. Because the induction and maintenance of peripheral immune tolerance are dependent on the orchestra playing by all type of those cell populations. To date a peripheral immune tolerance-based immunotherapeutic agent using an agonist to rebuild the tolerance through both pathways of PD-1/PD-L1 and Fc-gamma/Fc-gamma receptors has not yet been developed. Therefore, there is a need to develop a therapeutic reagent that the therapeutic effect not only targeting the autoreactive T cells and B cells but also targeting the inappropriately activated monocytes/macrophages and dendritic cells in inflammatory tissues, meanwhile, such reagent will avoid the causes of antibody dependent cell-mediated cytotoxicity (ADCC) and complement dependent cytotoxicity (CDC) in vivo due to its feature of biding to the activation of Fc receptor of Fc-gammaRI. Thus, when Ig chimeric proteins are used as an agent for treating an autoimmune disease or as an agent for inducing immune tolerance in organ transplantation, they cannot play the role of inhibiting inflammatory responses, and may rather aggravate inflammation.

2. SUMMARY OF THE INVENTION

In first aspect, the invention provides a bispecific biologic (chimeric protein of PD-L1/FC-gammal) named BY-001, which is a composition of homomultimeric forms of dimer, tetramer and Hexamer, wherein the ratio of the forms is at 25% of dimer, 30% of tetramer and 45% of Hexamer respectively.

In second aspect, current invention provides the demonstrations of bispecific function of BY-001 that aggregated PD-L1 can trigger the pathway of PD-1 to decrease the cytokine production from activated T cell line (jurkate cell expressing PD-1), and also the aggregated Fc-gammal shows the suppressive effect on monocyte/macrophage cell line (THP-1 cell expressing Fc-gammalRI & II) and erythroid cell line (K562 cell expressing Fc-gammalRII).

In third aspect, the present invention also demonstrates that the functional features of both the domains PD-L1 and Fc-gammal in BY-001 fully inherit their characteristics in their parental proteins that have been confirmed in vitro and in vivo that published in highly recognized scientific journals. Therefore, an obvious perspective emerges that the BY-001 of the present invention is potential for a pharmaceutical composition for treating an autoimmune disease caused by abnormal regulation of an immune response or preventing the rejection of allografts.

3. DISCLOSURE

3.1. Technical Problem and Solution

An object of the present invention is to provide BY-001 (a composition of bifunctional homomultimeric forms chimeric protein PD-L1/Fc-gammal) comprises the forms of dimer, tetramer and Hexamer at the ratio of 25%, 30% and 45%, wherein monomer form of chimeric protein PD-L1/Fc-gammal consists of two distinct domains. The amino acids of cysteine in the region of immunoglobulin Fc-gammal are kept in order to form the multimeric PD-L1/Fc-gammal, such homomultimeric form provides the aggregated Fc-gammal (BY-001) for binding to Fc-gammaRIIB instead of Fc-gammaRI. Another object of the present invention is to provide the aggregated form (BY-001) of extracellular domain of PD-L1 protein, which shows an excellent regulating effect on activity of T cells. Third object of the present invention is to provide the aggregated form of Fc-gammal region, which binds only to Fc-gammalRIIA and B and suppresses the production of pro-inflammatory factors in monocyte/macrophages and pre-erythrocytes.

3.1. Advantageous Effects

BY-001 of the present invention is a composition of chimeric protein PD-L1/Fc-gammal in the forms of dimer, tetramer and Hexamer. Such aggregated state of the chimeric protein PD-L1/Fc-gammal displays higher regulatory efficacy to PD1 and Fc-gammaRII. Therefore, it is more potential to regulate the activities of T cells including Th cells, cytotoxic-T cells and B cells during the active stage of autoimmunity, as well as to regulate the activities of monocytes/macrophages, dendritic cells and iTreg cells to restore and maintain the peripheral immune tolerance. Thereafter, the BY-001 of the present invention is potential for a pharmaceutical composition for treating an autoimmune disease caused by abnormal regulation of an immune response or preventing the rejection of allografts.

4. DESCRIPTION OF DRAWING

FIG. 1. Design for Chimeric Peptide of PD-1L/Fc-gammal (BY-001) and Its Amino Acid Sequence of SEQ ID NO: 2.

A. Schematic diagram for the design of chimeric protein PD-L1/Fc-gmmal consisting of extracellular portion of human PD-L1 and constant region of human IgG1 Fc. Please be noted: 1). Cysteines in V-set, C-set and IgG1Fc regions are kept for the —S—S— "disulfide" bond to form the advanced structure forms. 2). PD-L1/FC1 is 449 amino acid in total 3). The signal peptide of PD-L1 comprises amino acids 1-18, which will be digested when the protein secrets into culture medium. Therefore, the purified PD-L1/Fc-gammal of current invention contains 431 amino acids in total. 4). immunoglobulin V like region (V-set, 19.about.127 amino-acids, exon-2) 5). immunoglobulin constant like region (C-set, 133.about.220 amino-acids, exon 3) 6). human IgG1 heavy chain constant domain (C region, 221.sup.-449) is the region of Fc-gammal.

B. The AA sequence of PD-L1 contained in chimeric protein PD-L1/Fc-gammal. The sequence highlighted in yellow is the part of signal sequence for leading the protein toward the secretory pathway, which is cut away as the protein released to medium. The sequence highlighted in shadow is the region of Fc-gammal. For the detail about the sequence of SEQ ID NO:2, please refer to the information of file "BY-001sequence_ST25".

FIG. 2. Visualized Protein of BY-001 in SDS-Page Gel and Western-Blot DNA fragment encoding amino acid sequence of SEQ ID NO:2 was inserted into vector of pFUSE-hIgG1-Fc-gammalpurchased from INVIVOGEN USA, 10515 Vista Sorrento Pkwy, San Diego, Calif. 92121, USA. The DNA of pFuse-PD-L1/Fc-gammal was transfected with 293 cells. Monofinity A Column Purification (GenScript, 860 Centennial Avenue, Piscataway, N.J. 08854) was utilized to purify the BY-001 from the supernatants of 293 cell culture. The molecular wieght of expected protein in monomeric form is about 60 kilodalton (KD). Westen blot system was used for the analysis of protein product. Reducing and nonreducing condition (without dithiothreitol (DTT) for the former, with DTT for the latter) were applied for breaking up the disulfide bounds in advanced structure of BY-001.

A. SDS-page gel, Coommassie blue staining. Lane M1: Protein Marker Cat. No. 3452, Lane 1: BY-001 at Reducing condition (monomer), Lane 2: BY-001 at non-reducing condition (no monomer, but dimer, tetramer and Hexamer).

B. Western blot probed with Primary antibody: Goat Anti-Human IgG-HRP. Lane M2: Protein Marker, GenScript, Cat. No. M00521, Lane P: Human IgG1, Kappa (Sigma, Cat. No. 15154) as a positive control. Lane 1, monomer of PD-11/Fc-gammal band at nonreducing condition; Lane 2, multimeric forms of BY-001, dimer, tetramer and hexamer.

C. Western blot probed with Human PD-L1/B7-H1 Antibody (R&D, Cat. No. AF156). Lane M2: Protein Marker, GenScript, Cat. No. M00521; Lane 1, monomer of PD-11/Fc-gammal band at nonreducing condition; Lane 2, multimeric forms of BY-001, dimer, tetramer and hexamer.

D. Diagrams of the BY-001, cartoons of D, E and F are the graphic view for illustration of BY-001 at forms of dimer, tetramer and hexamer.

FIG. 3. BY-001 suppresses IL-2 production from Jurkate cell line Jurkate (from ATCC, USA) is a T cell line generated from human T-cell leukemia. CD3, CD28 and PD-1 are molecules expressed on the cell surface. OKT3 is an antibody against CD3, and its binding and cross-linking will activate T cells. CD28 is a receptor for co-stimulatory molecule B7 family. The association of anti-CD28 with CD28 will greatly enhance T cell activation based on OKT3 stimulation in vitro. IL-2 production is one of the biomarkers commonly to indicate T cell activation. The goal of this experiment is to validate and demonstrate the function of BY-001 in regulation of T cell activation in vitro. 5 ug/ml of OKT3 (Anti-human CD3, Clone OKT3, BD bioscience) was coated onto 96-well, U bottom micro-plate for overnight at 4.degree. C. Cell suspension of Jurkate cells at 3 million/ml is in RPM1164 medium with 10% FBS.

A. 100 ul of Cell suspension jurkate at 3 million/ml was added into each well hereafter, BY-001 was added into wells according to designed. The plate was kept in incubator at 37.degree. C. and 5% CO.sub.2 overnight. The culture supernatants were harvested from wells for the measurement of IL-2 production. Human IL-2 High Sensitivity ELISA Kit (eBioscience, 1030 Vienna, Austria) was used for the measurement of IL-2. The results indicate that BY-001 inhibits the IL-2 production effectively at the starting concentration (0.1 ug/ml) of BY-001. CD3 signal along (without the CD28 second signal) the inhibition was 87.5% at concentration of 0.1 ug/ml of BY-001, such inhibition was persistent from the concentrations of 0.1 ug/ml to 1 ug/ml.

B. Anti-human CD28 (BD bioscience, Clone CD28.2) mixed at 2 ug/ml into same jurkate cell suspension solution as used in (A). The plate was incubated at 37.degree. C. and 5% CO.sub.2 for overnight. The culture supernatants were harvested from wells for the measurement of IL-2 production by following the method in (A). The results indicate that TCR signal with the help of co-stimulator signal make Jurkate cell produces higher level of IL-2 (from 30 pg/ml at OKT3 along to 60 pg/ml at OKT3+anti-CD28), however it makes BY-001 inhibit IL-2 production as a gradient decent pattern at the concentration (0.5 to 2 ug/ml), the inhibitory rate become to be 13.1% at 0.5 ug/ml, 43% at 1.0 ug/ml to 67.6% at 2 ug/ml of BY-001.

FIG. 4. BY-001 suppresses IL-2 production from PBMC human primary cells The PBMC was obtained from healthy human donor. PBMC are cells containing only mononuclear in their cell. Among the PBMC, CD3 is expressed on all T cells, while CD3 and CD28 double positive T cells account for the majority of all T cells. B7 family and PD-1 are expressed on most of the PBMC cell surface. Fc receptor is expressed on dendritic cell, monocyte, etc. The goal of this experiment is to validate and demonstrate that BY-001 functions as a mediator in regulation of T cell activation in human primary cell, by which to indicate the great opportunity of success in clinical trial.

The 96-well plate was coated with 3 ug/ml of OKT3 at 4.degree. C. for overnight. 100 ul of Jurkate cell solution at 3 million/ml in the presence or no presence of Anti-human CD28 at 2 ug/ml were added into wells. The plate was kept in incubator at 37.degree. C. and 5% CO.sub.2 for overnight, supernatants were collected from the wells for IL-2 detection with Human IL-2 High Sensitivity ELISA Kit.

A. CD3 signal along (without the CD28 second signal) the inhibition was 90.8% at concentration of 0.25 ug/ml of BY-001, the inhibition is persistent at concentrations of BY-001 from 0.25 to 4 ug/ml.

B. CD3 signal together with the CD28 second signal the inhibition pattern became to be gradient decent from the inhibitory rate 17.5% at 0.25 ug/ml to 74.1% at 4 ug/ml of BY-001.

FIG. 5 BY-001 regulates BY-001 regulates IL-4 and TGF-betta production from K562 cell K562 cell (from ATCC, USA) is pre-erythrocyte generated from human myelogenous leukemia (of the erythroleukemia type) in which no CD3, CD28 and PD-1 molecules are expressed. However, it was reported that only Fc-gammal receptor II are expressed on its cell surface but no Fc-gammal receptor I. Therefore, only aggregated Fc-gammal are capable to binding to and triggering the Fc-gammal/Fc-GammalRII pathway. To determine the function of aggreged Fc-gammal of BY-001 we measured the regulation of IL-4 and TGF-betta production in K562 cells. Apparently, the signaling transferred in this demonstration is suppressive.

A. The basal level of IL-4 production in K562 is high (84 pg/ml). Addition of BY-00-1 according to designed into the cells culture decreases the IL-4 level. The inhibition is sufficient at concentration of 4 ug/ml of BY-001, which indicates that aggregated Fc-gammal bind to Fc-gammal/Fc-GammalRII and trigger the inhibitory pathway.

B. The basal level of TGF-betta production in K562 is high (1250 pg/ml). Addition of BY-00-1 according to designed into the cells culture decreases the TGF-betta level. The inhibition is sufficient at concentration of 2 and 4 ug/ml of BY-001, which indicates that aggregated Fc-gammal bind to Fc-gammal/Fc-GammalRII and trigger the inhibitory pathway.

C. The diagram for BY-001 binding to and triggering the Fc-gammaRII, thereafter to deliver the suppressive signal. ITAM stands for immunoreceptor tyrosine-based activation motif in which the tyrosine residues are phosphorylated upon the binding between Fc-gammal and Fc-gammalRII. While ITIM stands for the immunoreceptor tyrosine-based inhibitory motif in which the tyrosine residues are phosphorylated, thereafter the phosphatase SHIP1 or 2 is activated to dephosphorylate the phosphorylated tyrosine in ITAM of Fc-gammaRIIA or C via the crosslinking of bound Fc-gammals of BY-001.

FIG. 6. BY-001 regulates the IL-4 and TGF-betta production from THP-1 cells THP-1 cell (from ATCC, USA) is THP-1 is a human monocytic cell line derived from acute monocytic leukemia in which no CD3, CD28 and PD-1 molecules are expressed. However, it was reported that both Fc-gammal receptor I and II are expressed on its cell surface. To date, it has been believed that Fc region of monomeric antibody is high affinity to Fc-gammalRI but with very low avidity to Fc-gammaRII. In contrast, the Fc portion of antigen-antibody complex binds to Fc-gammaRII instead of Fc-gammaRI. Therefore, to determine the efficacy of aggregated Fc-gammal of BY-001 in binding to and triggering the Fc-gammal/Fc-gammalRII pathway, we measured the regulation of IL-4 and TGF-betta production in THP-1 cells. Apparently, the signaling transferred in this demonstration is suppressive, which indicates also that the aggregated Fc-gammal of BY-001 triggers the inhibitory pathway of Fc-gamma/Fc-gammaRIIB A. The basal level of IL-4 production in THP-1 is high (86 pg/ml). Addition of BY-00-1 according to designed into the cells culture decreases the IL-4 level. The inhibitions are sufficient at concentration of 2 and 4 ug/ml of BY-001, which indicates that aggregated Fc-gammal bind to Fc-gammal/Fc-GammalRII and trigger the inhibitory pathway only.

B. The basal level of TGF-betta production in THP-1 is high (485 pg/ml). Addition of BY-00-1 according to designed into the cells culture decreases the TGF-betta level. The inhibition is observed at concentration of 2 and 4 ug/ml of BY-001, which indicates that aggregated Fc-gammal bind to Fc-gammal/Fc-GammalRII and trigger the inhibitory pathway only.

C. The diagram for BY-001 binding to and triggering the Fc-gammaRII, thereafter to deliver the suppressive signal. ITAM stands for immunoreceptor tyrosine-based activation motif in which the tyrosine residues are phosphorylated upon the binding between Fc-gammal and Fc-gammalRII. While ITIM stands for the immunoreceptor tyrosine-based inhibitory motif in which the tyrosine residues are phosphorylated, thereafter the phosphatase SHIP1 or 2 is activated to dephosphorylate the phosphorylated tyrosine in ITAM of Fc-gammaRIIA or C via the crosslinking of bound Fc-gammals of BY-001. Apparently, the Fc-gammaRI has no effect on the inhibition, which is benefited for BY-001, hereinafter, in dealing with autoimmunity.

FIG. 7 Advanced structural difference between BY-001 and antigen-antibody complex specific antibodies associate with antigen with electrostatic attraction and hydrophobic bonds or hydrogen bonds, which are separated easily in SDS page gel of protein electrophoresis. While the PD-L1/Fc-gammal of present invention bound together with disulfide bound (S--S) without the component of antigen, and the S--S bound only can be broken up under the of reducing condition (by adding DTT) in SDS page gel of protein electrophoresis.

A. The diagram is the dimer of BY-001 bound together by S--S bound

B. The diagram is the tetramer of BY-001 bound together by S--S bound

C. the diagram is the hexamer of BY-001 bound together by S--S bound

D. the diagram is the antigen-antibody complex

FIG. 8 Expected mechanism for BY-001 to rebuild the peripheral immune tolerance Genetic alterations (gene mutation or polymorphism) may cause the individual difficult to maintain the peripheral tolerance of immunity. The dendritic cells, macrophages, T cells are become to be very fragile to resist the alteration of microenvironment, then easily to be activated inappropriately. The outcome is the generation of auto-cytotoxic T cell against self-tissues. The addition of BY-001 will directly reduce the activity of cytotoxic T cells by which to induce the auto-cytotoxic T cell anergy, on the other hand, BY-001 will also regulate the activities of Th cell, Treg cells and dendritic cells, macrophages which is critical to rebuilt peripheral immune tolerance.

5. DETAILED DESCRIPTION OF THE INVENTION 5.1. Definitions: Prior to describing the invention in more detail the following definitions are provided. Unless otherwise stated, all technical and scientific terms used herein have the same meanings as commonly understood by one of ordinary skill in the art to which this invention belongs. Any methods and materials with similar or equivalent function to those described herein can be used in the practice or testing of the present invention. Methods, devices, and materials suitable for such uses are now described. All publications cited herein are incorporated herein by reference in their entirety for the purpose of describing and disclosing the methodologies, reagents, and tools reported in the publications that might be used in connection with the invention.

In accordance with the object of the present invention, in one aspect, there is provided a fusion protein comprising the extracellular domain of PD-L1 protein or a fragment thereof and a human immunoglobulin Fc-gammal region ("PD-L1/Fc-gammal chimeric protein," "PD-L1/Fc-gammal protein," "PD-L1 chimeric protein" or "chimeric protein"). The extracellular domain of PD-L1 may be a polypeptide comprising an immunoglobulin V (V-set) like domain of PD-L1 and an immunoglobulin C (C-set) like domain of PD-L1. The extracellular domain of PD-L1 is a domain exposed outside a cell membrane, and may be a polypeptide comprising the amino acids at positions 19 to 220 of sequence of SEQ ID NO:2. In addition, the extracellular domain of PD-L1 or a fragment thereof may be of human origin. In addition, the extracellular domain of PD-L1 may have about 70%, 75%, 80%, 85%, 90%, 91%, 92%, 93%, 94%, 95%, 96%, 97%, 98%, 99% or more homology to the polypeptide sequence consisting of the amino acids at positions 19 to 220 of sequence of SEQ ID NO:2. In addition, Human IgG1 heavy chain constant domain (C region, 221.about.449) of the sequence of SEQ ID NO:2 is the region of Fc-gammal. All the Cysteines in V-set and C-set and human immunoglobulin Fc-gammal region of PD-L1/Fc-gammal thereof are kept in current invention for the —S—S— "disulfide" bond to form the advanced structure.

As used herein, the term "BY-001" refers to a composition of homomultimeric forms of bifunctional chimeric protein PD-L1/Fc-gammal at the ratio of 25% of dimer, 30% of tetramer and 45% of Hexamer.

As used herein, the term "immune cell" includes cells that are of hematopoietic origin and that play a role in the immune response, such as B cells, T cells, dendritic cells, natural killer cells, monocytes and macrophages, etc.

As used herein, the term "T cell" includes CD4+Th1 and Th2 cells, CD3+ and CD8+ cytotoxic T cells including self-reactive T cells, CD25+ and FOX3+ Treg cells and inducible Treg cells (iTreg).

As used herein, the term "B cells" refers to the B cell potential to producing the antibodies including the self-reactive antibodies.

As used herein, the term "aggregated PD-L1" refers to the extracellular portion of PD-L1 of human or mouse origin at the aggregated state thereof.

As used herein, the term "aggregated Fc-gammal" refers to the regions of hinge, CH2 and CH3 of human IgG1 heavy chain of human or mouse origin at the aggregated state thereof, in addition, any peptide combined to the regions of hinge, CH2 and CH3 of human IgG1 heavy chain of human or mouse origin at the aggregated state thereof is include.

As used herein, the term "inhibitory signal" refers to a signal transmitted via an inhibitory receptor molecule on an immune cell. Such as CTLA-4, PD-1 and Fc-gammaRIIB 5.2. Mode for Invention Hereinafter, the invention is explained in accordance with the examples to further illustrate the application without limiting its scope.

In accordance with the object of the present invention, first structure of protein in one aspect, there is provided bifunctional chimeric protein in first structure of protein comprising a first function domain, the extracellular domain of PD-L1 protein or a fragment thereof and a second function domain, the human immunoglobulin Fc-gammal region. The bifunctional chimeric protein of current invention is stated as "PD-L1/Fc-gammal chimeric protein" or "PD-L1/Fc-gammal protein" or "PD-L1 chimeric protein" or "chimeric protein". The extracellular domain of PD-L1 may be a polypeptide comprising an immunoglobulin V (V-set) like domain of PD-L1 and an immunoglobulin C (C-set) like domain of PD-L1. The extracellular domain of PD-L1 is a domain exposed outside a cell membrane, and may be a polypeptide comprising the amino acids at positions 19 to 220 of sequence of SEQ ID NO:2. In addition, the extracellular domain of PD-L1 or a fragment thereof may be of human origin. In addition, the extracellular domain of PD-L1 may have about 70%, 75%, 80%, 85%, 90%, 91%, 92%, 93%, 94%, 95%, 96%, 97%, 98%, 99% or more homology to the polypeptide sequence consisting of the amino acids at positions 19 to 220 of sequence of SEQ ID NO:2. In addition, Human IgG1 heavy chain constant domain (C region, 221.about.449) of the sequence of SEQ ID NO:2 is the region of Fc-gammal.

The present invention provided, advanced structure of protein in another aspect, is bifunctional chimeric protein in advanced structure of protein comprising a composition of homomultimer of dimer, tetramer and hexamer of PD-L1/Fc-gammal chimeric protein (BY-001). All the Cysteines in V-set and C-set and human immunoglobulin Fc-gammal region of PD-L1/Fc-gammal thereof are kept in current invention for the —S—S— "disulfide" bond to form the advanced structure. Hence, once the PD-L1 is fused to second domain components Fc-gammal, it is a complex naturally composed in dimer, tetramer and Hexamer, in fact PD-L1 dimer, tetramer and Hexamer are formed, on the other hand, Fc-gammal dimer, tetramer and Hexamer are formed also, for example as presented in FIG. 2.

To date, the subsets of immune cells of activated T cells, B cells and dendritic cells are related to the autoimmunity and rejection of allografts, while monocytes/macrophages are one of the key subsets related to inflammatory reaction, particularly to the chronic inflammation. It has highly recognized that the cell signaling pathways PD-1/PD-L1 and Fc-gammaRII/Fc-gamma are crucial in the regulation of functions of the subsets of immune cells mentioned above.

Under physiological condition, PD-1 is expressed in activated T cells and B cells and is bound and triggered by monomeric PD-L1, thereafter, the PD-1/PD-L1 pathway delivers the cell signaling of immune checkpoint. Thus PD-1/PD-L1 axis is one of the pathways that exert the key roles in the establishing and maintenance of immune tolerance. The provided in current invention is the PD-L1 in chimeric protein at its aggregated state and is expected to act on the PD-1 signaling axis. To validate the function of PD-L1 at its aggregated forms as stated (FIG. 2) in current invention, in one embodiment as presented in FIG. 3 and FIG. 4 of current invention, the present invention provides validation that PD-1 on immune cells is activated by the aggregated form of PD-L1 (BY-001), thereafter to deliver the cell signaling of immune checkpoint. The bifunctional chimeric protein PD-L1/Fc-gammal comprising a first domain PD-L1 that binds to and triggers PD-1. For example, as shown in current invention, BY-001 inhibits the IL-2 production from the Jurkate cells (FIG. 3) and human PBMCs of healthy donor (FIG. 4) after the treatment with either OKT3 antibody or CKT3 antibody+CD28 antibody. OKT3 antibody along or together with CD28 antibody as the co-stimulator are commonly used to trigger TCR signaling for the activation of CD3+ T cells. IL-2 production is one of the biomarkers commonly to indicate T cell activation. It has commonly believed that inflammatory reaction in autoimmunity or rejection of allografts are caused by inappropriate activation of the self-reactive T cells and self-reactive B cells due to the peripheral immune tolerance breakdown [1-3]). The current methods in the treatment of autoimmune diseases or protection of allografts are to suppress the activity of the mentioned self-reactive T cells and self-reactive B cells [5, 35]. To date, it has believed that cell surface receptor of PD-1 is expressed only in activated T cells and B cells [35]. The association between PD-1 and PD-L1 induces the activated T anergy cell or B cell anergy or apoptosis, or alternatively the association induces the differentiation of Treg cell from Th cell [36]. Therefore, the current invention provided homomultimeric forms of PD-L1/Fc-gammal (BY-001), a novel concept of soluble chimeric proteins, is potential to treat certain immune and inflammatory disorders in one dimension.

According to the ability to activate or suppress the immune response Fc-gamma receptors are divided in two classes: hFc-gammaRI, hFc-gammaRIIA and hFc-gammaRIIIA are activating receptors via the cytoplasmic ITAM (immunoreceptor tyrosine-based activation motif), whereas hFc-gammaRIIB is suppressing receptor via the cytoplasmic ITIM (immunoreceptor tyrosine-based inhibitory motif) [37]. Fc-gammaRI is a high-affinity receptor that binds to only monomeric IgG and is expressed constitutively in dendritic cells, monocytes and macrophages in both human and mice[38]. In contrast to Fc-gammaRI, the other three types express in most of the immune cell populations, except the B cells, and exhibit affinity to Fc-gamma of IgGs in antigen-antibody complex, among them Fc-gammaRIIB exerts the suppressive signaling through its binding with one Fc-gamma and crosslinking others Fc-gammaRIIA with others Fc-gamma in antigen-antibody complex. Furthermore, Fc-gammaRIIB is expressed on B cell and appears to function in a B cell-autonomous manner to regulate autoreactive cells in the periphery. There have been extensively reported that Fc-gammaRII plays key role in autoimmunity and inflammatory disorders. Fc-gammaRII/Fc-gamma axis dominates the activation and chemo-cytokines production profile of dendritic cells and monocytes/macrophages, which is critical for the process of inflammation, and also is the key role in maintenance of immune tolerance. The provided in current invention is the Fc-gammal in chimeric protein at its aggregated state and is expected to act on the Fc-gammaRII signaling axis.

To validate the function of Fc-gammal at its aggregated forms as stated (FIG. 2) in current invention, in another embodiment, as a novel concept of soluble chimeric proteins, presented in FIG. 5 and FIG. 6 of current invention, the present invention provides validation that Fc-gammaRIIB on immune cells is activated by the aggregated form of Fc-gammal (BY-001), thereafter to deliver the suppressive cell signaling to immune cells. In current invention, the artificially aggregated form PD-L1/Fc-gammal (BY-001) in tetramer and hexamer are distinct from the Fc form in Ag-Ab complex in structure according to diagram in FIG. 7 of current invention. As shown in current invention, for example, BY-001 inhibits the IL-4 and TGF-betta production from the K562 cells and THP-1 cells. It was reported that K562 cells express ortly Fc-gamma receptor II [39], while THP-1 cells express both Fc-gamma receptor I and II on the cell surface[40]. Apparently, the activating receptor of Fc-gammaRI on THP-1 cell didn't influence the suppressive pathway of Fc-gammaRIIB/Fc-gammal. The machinery of suppressive pathway may comprise Fc-gammal bound with Fc-gammaRIIB and others Fc-gammal in multimeric form crosslinked the Fc-gammaRIIA or RITC, thereafter, the inhibitory signaling is delivered and the activity of the cells are decreased through the pathway.

Collectively, BY-001 exerts dual functions that in one hand binds to and triggers the PD-1 pathway through multimeric PD-L1, and on the other hand binds to Fc-gammalRIIB through multimeric Fc-gammal to trigger the suppressive signaling into the cells. Thereafter, BY-001 is capable to regulate the subsets of immune cells activated T cells and B cells, meanwhile to regulate the subsets of dendritic cell and monocytes/macrophages, the immune cell populations tightly relate to autoimmunity and protection of allografts. Therefore, BY-001 is potential to treat certain immune and inflammatory disorders. In the setting of autoimmune, alloimmune and inflammatory diseases, the homomultimeric forms of chimeric protein of this invention can reduce autoimmune, alloimmune and inflammatory manifestations by one or more mechanisms. For example, the PD-L1 extracellular domain in homomultimeric forms of chimeric protein of this invention can bind to the PD-1 on immune cell, such as an activated T cell or pre-B cell; while the second domain in homomultimeric forms of chimeric protein binds to and cross-links the FC receptors that express on dendritic cell and macrophage and other immune cell bearing Fc-gammaRII or RIII, etc.. Through these binding and cross-linking events, the receptors PD-1 for the first domain trigger the T cell anergy, repress the B cell maturation, differentiation of Treg cells and regulatory dendritic cells; the FC receptors for second domain of the chimeric protein may inhibit the activated dendritic cell and macrophage in the inflammatory location. All these events are critical to induce and maintain the immune tolerance of the body.

In addition, once the FC-gammal contained in chimeric protein anchored to FC receptor on cell surface of dendritic cell and macrophage, now membrane-anchored, therefore, the chimeric protein of the present invention may mediate its activity by spanning two neighboring cells, and thereby establish an immune tolerant microenvironment at inflammatory site. Alternatively, for example, a PD-L1 containing chimeric protein can bind to the B7-1 costimulator on an antigen-presenting cell, thereby interfering with its costimulatory, immune-activating function.

As indicated in schematic diagram of FIG. 8, BY-001 is potential for the treatment of autoimmune diseases and protection of allografts. For example, type 1 diabetes (T1D, Systemic Lupus Erythematosus (SLE), Rheumatoid Arthritis (RA) and inflammatory bowel disease (IBD) (including ulcerative colitis (UC) and Crohn's disease (CD)), multiple sclerosis (MS), scleroderma, and other diseases and disorders, such as PV (pemphigus vulgaris), psoriasis, atopic dermatitis, celiac disease, Chronic Obstructive Lung disease, Hashimoto's thyroiditis, Graves' disease (thyroid), Sjogren's syndrome, Guillain-Barre syndrome, Goodpasture's syndrome, Addison's disease, Wegener's granulomatosis, primary biliary sclerosis, sclerosing cholangitis, autoimmune hepatitis, polymyalgia rheumatica. Raynaud's phenomenon, temporal arteritis, giant cell arteritis, autoimmune hemolytic anemia, pernicious anemia, polyarteritis nodosa. Behcet's disease, primary bilary cirrhosis, uveitis, myocarditis, rheumatic fever, ankylosing spondylitis, glomerulenephritis, sarcoidosis, dermatomyositis, myasthenia gravis, polymyositis, alopecia areata, and vitilgo.

7. Field of the Invention

The present invention relates to the advanced structure of chimeric protein PD-L1/Fc-gammal composed of homomultimeric forms (BY-001), wherein the first domain, such as PD-L1, at the aggregated state binds to and triggers the PD-1 and the second domain, such as Fc-gammal, at the aggregated state binds to and triggers Fc-gammal receptor type II.

8. REFERENCES

1. Davidson, A. and B. Diamond, Autoimmune diseases. N Engl J Med, 2001. 345(5): p. 340-50.
2. Goding, J. W., Autoimmune diseases. N Engl J Med, 2001. 345(23): p. 1707-8.
3. Bluestone, J. A., Mechanisms of tolerance. Immunol Rev, 2011. 241(1): p. 5-19.
4. Smilek, D. E., M. R. Ehlers, and G. T. Nepom, Restoring the balance: immunotherapeutic combinations for autoimmune disease. Dis Model Mech, 2014. 7(5): p. 503-13.
5. Brackmann, H. H., et al., Immune tolerance induction: What have we learned over time? Haemophilia, 2018. 24 Sunni 3: p. 3-14.
6. Boonman, Z. F., et al., Maintenance of immune tolerance depends on normal tissue homeostasis. J Immunol, 2005. 175(7): p. 4247-54.
7. Schep, S. J., et al., Review of immune tolerance induction in hemophilia A. Blood Rev, 2018. 32(4): p. 326-338.
8. Bardhan, K., T. Anagnostou, and V. A. Boussiotis, The PD1:PD-L1/2 Pathway from Discovery to Clinical Implementation. Front Immunol, 2016. 7: p. 550.
9. Thibult, M. L., et al., PD-1 is a novel regulator of human B-cell activation. Int Immunol, 2013. 25(2): p. 129-37.

10. Francisco, L. M., P. T. Sage, and A. H. Sharpe, The PD-1 pathway in tolerance and autoimmunity. Immunol Rev, 2010. 236: p. 219-42.
11. Amarnath, S., et al., The PDL1-PD1 axis converts human TH1 cells into regulatory T cells. Sci Trans) Med, 2011. 3(111): p. 111ra120.
12. Zhu, X. and J. Lang, Soluble PD-1 and PD-L1: predictive and prognostic significance in cancer. Oncotarget, 2017. 8(57): p. 97671-97682.
13. Li, Y., et al., Role of soluble programmed death-1 (sPD-1) and sPD-ligand 1 in patients with cystic echinococcosis. Exp Ther Med, 2016. 11(1): p. 251-256.
14. Alsaab, H. O., et al., PD-1 and PD-L1 Checkpoint Signaling Inhibition for Cancer Immunotherapy: Mechanism, Combinations, and Clinical Outcome. Front Pharmacol, 2017. 8: p. 561.
15. Zamani, M. R., et al., PD-1/PD-L and autoimmunity: A growing relationship. Cell Immunol, 2016. 310: p. 27-41.
16. Liao, W., et al., The Systemic Activation of Programmed Death 1-PD-L1 Axis Protects Systemic Lupus Erythematosus Model from Nephritis. Am J Nephrol, 2017. 46(5): p. 371-379.
17. Nishimura, H., et al., Autoimmune dilated cardiomyopathy in PD-1 receptor-deficient mice. Science, 2001. 291 (5502): p. 319-22.
18. Dinesh, R. K., B. H. Hahn, and R. P. Singh, PD-1, gender, and autoimmunity. Autoimmun Rev, 2010. 9(8): p. 583-7.
19. Wang, C. J., et al., Protective role of programmed death 1 ligand 1 (PD-L1) in nonobese diabetic mice: the paradox in transgenic models. Diabetes, 2008. 57(7): p. 1861-9.
20. Martinov, T., et al., PD-1 pathway-mediated regulation of islet-specific CD4(+) T cell subsets in autoimmune diabetes. Immunoendocrinology (Houst), 2016. 3.
21. Constantinescu, C. S., et al., Experimental autoimmune encephalomyelitis (EAE) as a model for multiple sclerosis (MS). Br J Pharmacol, 2011. 164(4): p. 1079-106.
22. Keir, M. E., et al., Tissue expression of PD-L1 mediates peripheral T cell tolerance. J Exp Med, 2006. 203(4): p. 883-95.
23. Shashidharamurthy, R., et al., Dynamics of the interaction of human IgG subtype immune complexes with cells expressing R and H allelic forms of a low-affinity Fc gamma receptor CD32A. J Immunol, 2009. 183(12): p. 8216-24.
24. Pritchard, N. R. and K. G. Smith, B cell inhibitory receptors and autoimmunity. Immunology, 2003. 108(3): p. 263-73.
25. Chu, S. Y., et al., Inhibition of B cell receptor-mediated activation of primary human B cells by coengagement of CD19 and FcgammaRIIb with Fc-engineered antibodies. Mol Immunol, 2008. 45(15): p. 3926-33.
26. Bruhns, P. and J. L. Teillaud, Inhibitory IgG Receptor-Expressing Cells: The Must-Have Accessory for Anti-CD40 Immunomodulatory mAb Efficacy. Cancer Cell, 2016. 29(6): p. 771-773.
27. Desai, D. D., et al., Fc gamma receptor IIB on dendritic cells enforces peripheral tolerance by inhibiting effector T cell responses. J Immunol, 2007. 178(10): p. 6217-26.
28. Dhodapkar, K. M., et al., Selective blockade of the inhibitory Fcgamma receptor (FcgammaRIIB) in human dendritic cells and monocytes induces a type I interferon response program. J Exp Med, 2007. 204(6): p. 1359-69.
29. Gordon, J. R., et al., Regulatory dendritic cells for immunotherapy in immunologic diseases. Front Immunol, 2014. 5: p. 7.
30. Smith, K. G. and M. R. Clatworthy, FcgammaRIIB in autoimmunity and infection: evolutionary and therapeutic implications. Nat Rev Immunol, 2010. 10(5): p. 328-43.
31. Nakamura, A. and T. Takai, A role of FcgammaRIIB in the development of collagen-induced arthritis. Biomed Pharmacother, 2004. 58(5): p. 292-8.
32. Callaghan, C. J., et al., Regulation of allograft survival by inhibitory FcgammaRIIb signaling. J Immunol, 2012. 189(12): p. 5694-702.
33. Watkins, A. A., et al., IRF5 deficiency ameliorates lupus but promotes atherosclerosis and metabolic dysfunction in a mouse model of lupus-associated atherosclerosis. J Immunol, 2015. 194(4): p. 1467-79.
34. Sage, A. P. and Z. Mallat, Readapting the adaptive immune response—therapeutic strategies for atherosclerosis. Br J Pharmacol, 2017. 174(22): p. 3926-3939.
35. Fife, B. T. and K. E. Pauken, The role of the PD-1 pathway in autoimmunity and peripheral tolerance. Ann N Y Acad Sci, 2011. 1217: p. 45-59.
36. Ulges, A., et al., Context- and Tissue-Specific Regulation of Immunity and Tolerance by Regulatory T Cells. Adv Immunol, 2016. 132: p. 1-46.
37. Roghanian, A., et al., New revelations from an old receptor: Immunoregulatory functions of the inhibitory Fc gamma receptor, FcgammaRIIB (CD32B). J Leukoc Biol, 2018.
38. Mancardi, D. A., et al., The high-affinity human IgG receptor FcgammaRI (CD64) promotes IgG-mediated inflammation, anaphylaxis, and antitumor immunotherapy. Blood, 2013. 121(9): p. 1563-73.
39. Chiofalo, M. S., et al., Subclass specificity of the Fc receptor for human IgG on K562. Cell Immunol, 1988. 114(2): p. 272-81.
40. Scholl, P. R., D. Ahern, and R. S. Geha, Protein tyrosine phosphorylation induced via the IgG receptors Fc gamma Ri and Fc gamma RII in the human monocytic cell line THP-1. J Immunol, 1992. 149(5): p. 1751-7.

The invention claimed is:

1. A chimeric protein consisting of the amino acid sequence of SEQ ID NO: 2.

2. A composition, comprising homomultimeric forms of the chimeric protein according to claim 1, wherein the homomultimeric forms comprise dimers, tetramers, hexamers, or a combination thereof.

3. The composition according to claim 2, wherein the percentage ratio of the dimers:tetramers: hexamers is 25%: 30%: 45%.

4. A method of treating CD3+ CD28+ immune cells in a subject, comprising administering the subject the composition according to claim 2.

5. A method of treating human peripheral blood monocyte (hPBMC) in a subject, comprising administering to the subject the composition according to claim 2.

6. A method of treating immune cells comprising immune cells bearing Fc-gammaRI and Fc-gammaRII in a subject, comprising administering to the subject the composition according to claim 2.

* * * * *

SEQUENCE LISTING

```
<160> NUMBER OF SEQ ID NOS: 2

<210> SEQ ID NO 1
<211> LENGTH: 1350
<212> TYPE: DNA
<213> ORGANISM: Homo sapiens

<400> SEQUENCE: 1
atgaggatat ttgctgtctt tatattcatg acctactggc atttgctgaa cgcatttact      60
gtcacggttc ccaaggacct atatgtggta gagtatggta gcaatatgac aattgaatgc     120
```

```
aaattcccag tagaaaaaca attagacctg gctgcactaa ttgtctattg ggaaatggag    180
gataagaaca ttattcaatt tgtgcatgga gaggaagacc tgaaggttca gcatagtagc    240
tacagacaga gggcccggct gttgaaggac cagctctccc tgggaaatgc tgcacttcag    300
atcacagatg tgaaattgca ggatgcaggg gtgtaccgct gcatgatcag ctatggtggt    360
gccgactaca agcgaattac tgtgaaagtc aatgccccat acaacaaaat caaccaaaga    420
attttggttg tggatccagt cacctctgaa catgaactga catgtcaggc tgagggctac    480
cccaaggccg aagtcatctg gacaagcagt gaccatcaag tcctgagtgg taagaccacc    540
accaccaatt ccaagagaga ggagaagctt ttcaatgtga ccagcacact gagaatcaac    600
acaacaacta atgagatttt ctactgcact tttaggagat tagatcctga ggaaaaccat    660
agatctgaca aaactcacac atgcccaccg tgcccagcac ctgaactcct gggggggaccg    720 tcagtcttcc tcttcccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020 gccaagggc agccccgaga accacaggtg tacaccctgc cccatcccg ggaggagatg   1080 accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctacagc aagctcaccg tggacaagag caggtggcag   1260
caggggaacg tcttctcatg ctccgtgatg cacgaggctc tgcacaacca ctacacgcag   1320
aagagcctct ccctgtctcc gggtaaatga                                    1350
```

<210> SEQ ID NO 2
<211> LENGTH: 449
<212> TYPE: PRT
<213> ORGANISM: Homo sapiens
<220> FEATURE:
<221> NAME/KEY: DOMAIN
<222> LOCATION: (19)..(449)

<400> SEQUENCE: 2

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val

```
            130                 135                 140
Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
                180                 185                 190

Val Thr Ser Thr Leu Arg Ile Asn Thr Thr Thr Asn Glu Ile Phe Tyr
                195                 200                 205

Cys Thr Phe Arg Arg Leu Asp Pro Glu Glu Asn His Arg Ser Asp Lys
                210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys
```